(12) United States Patent
Smith (10) Patent No.: US 9,227,015 B2
(45) Date of Patent: Jan. 5, 2016

(54) SPRING DRIVEN INJECTION DEVICE WITH TWIN CARTRIDGES

(75) Inventor: Christopher James Smith, Holmes Chapel (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 301 days.

(21) Appl. No.: 13/576,307

(22) PCT Filed: Feb. 15, 2011

(86) PCT No.: PCT/EP2011/052228
§ 371 (c)(1),
(2), (4) Date: Jan. 17, 2013

(87) PCT Pub. No.: WO2011/101351
PCT Pub. Date: Aug. 25, 2011

(65) Prior Publication Data
US 2013/0197447 A1   Aug. 1, 2013

Related U.S. Application Data

(60) Provisional application No. 61/305,438, filed on Feb. 17, 2010.

(30) Foreign Application Priority Data

Jul. 8, 2010   (EP) ..................... 10168931

(51) Int. Cl.
*A61M 5/19*   (2006.01)
*A61M 5/20*   (2006.01)
*A61M 5/24*   (2006.01)
*A61M 5/315*  (2006.01)

(52) U.S. Cl.
CPC . *A61M 5/19* (2013.01); *A61M 5/20* (2013.01); *A61M 5/3156* (2013.01); *A61M 5/31553* (2013.01); *A61M 5/31561* (2013.01); *A61M 5/31583* (2013.01); *A61M 5/31593* (2013.01); *A61M 5/24* (2013.01); *A61M 5/31543* (2013.01); *A61M 2005/2407* (2013.01)

(58) Field of Classification Search
CPC .......... A61M 5/19; A61M 5/20; A61M 5/24; A61M 5/31543; A61M 5/31553; A61M 5/3156; A61M 5/31583; A61M 5/31593; A61M 2005/2407
USPC ............. 604/82–83, 85–86, 89–90, 191, 232, 604/207–209, 211
See application file for complete search history.

(56) References Cited

U.S. PATENT DOCUMENTS 5,253,785 A * 10/1993 Haber et al. ..................... 222/43
5,271,527 A * 12/1993 Haber et al. ..................... 222/43
(Continued)

FOREIGN PATENT DOCUMENTS

DE     19930931 A1    1/2001
DE     10233925 A1    2/2004
(Continued)

*Primary Examiner* — Quynh-Nhu H Vu
(74) *Attorney, Agent, or Firm* — Fish & Richardson P.C.

(57) ABSTRACT

A semi-automatic injection device (12) is disclosed containing two reservoirs (6) of medicament, where a trigger (11) controls the unwinding of two torsional springs (18) to cause simultaneous injection of medicament from each reservoir through a needle adaptor configured with a 2 to 1 needle cannula arrangement.

13 Claims, 4 Drawing Sheets

(56) References Cited

U.S. PATENT DOCUMENTS

| | | | |
|---|---|---|---|
| 5,298,023 A * | 3/1994 | Haber et al. | 604/90 |
| 5,329,976 A * | 7/1994 | Haber et al. | 141/25 |
| 5,378,233 A * | 1/1995 | Haber et al. | 604/83 |
| 5,423,752 A | 6/1995 | Haber et al. | |
| 5,478,323 A * | 12/1995 | Westwood et al. | 604/191 |
| 5,505,704 A * | 4/1996 | Pawelka et al. | 604/191 |
| 5,584,815 A * | 12/1996 | Pawelka et al. | 604/191 |

FOREIGN PATENT DOCUMENTS

| | | |
|---|---|---|
| EP | 0710487 A2 | 5/1996 |
| WO | 2007063342 A1 | 6/2007 |
| WO | 2008087071 A1 | 7/2008 |

\* cited by examiner

SPRING DRIVEN INJECTION DEVICE WITH TWIN CARTRIDGES

CROSS REFERENCE TO RELATED APPLICATIONS

The present application is a 35 U.S.C. 371 National Application of PCT/EP2011/052228 filed Feb. 15, 2011, which claims priority to U.S. Application No. 61/305,438, filed Feb. 17, 2010 and European Patent Application No. 10168931.3, filed Jul. 8, 2010, the entire contents of which are incorporated entirely herein by reference.

This disclosure relates to an injection device, preferably a dual cartridge injection device. In particular, this disclosure relates to a device that may simultaneously inject a combination of doses of one or more medicaments from two cartridges through a single needle, particularly semi-automatically, when a user activates a trigger.

Multi-use injection devices are in common use for the delivery of injected medication. Such devices are needed so that a user may take more than one injected medication at a time, for example rapid acting & basal insulins, basal insulin & GLP-1 etc, without the need to perform multiple injections. It may not be desirable, for technical, medicament stability or therapeutic reasons, to provide these medications in a single combined form. For example, when mixing the two drugs each patient requires a different mix ratio or the mix ratio needs to vary from injection to injection depending on the patient's symptoms, state of health etc.

Conducting multiple injections is both inconvenient and uncomfortable for the user. Two separate devices must be carried, two needles must be attached and the skin is pierced twice. A dual cartridge injection device, capable of injecting two medications through a single delivery needle, would reduce the number of user steps and the number of times the skin is pierced. Furthermore, there may be a therapeutic advantage to delivering the two drugs to the same injection site. This would be very difficult, if not impossible, to achieve with two separate injections.

The art has recognized a need to inject two or more medications simultaneously and has disclosed injection devices that hold two cartridges of medication. One such device is disclosed in U.S. Pat. No. 5,584,815. However, attempts to simultaneously inject two medicaments, such as regular, fast acting insulin and long lasting insulin, have met with limited success, especially when the medication is forced to flow from the two cartridges through a manifold and out of a single cannula in fluid communication with the manifold. Blockage of the manifold and high injection force are two of the problems encountered by such previously proposed devices.

Accordingly, there still exists a strong need to provide users of such injection devices with an easy to use device that allows for the simultaneous injection of two or more medicaments and that provides a low injection force.

It is an object of this disclosure to provide a novel injection device, preferably an improved injection device.

This object may be achieved by the subject matter of the independent claim. Advantageous embodiments and refinements are the subject matter of the dependent claims.

This disclosure may, for example, facilitate solving the above-described problems by providing a, preferably semi-automatic, injection device where two or more medicaments housed in separate reservoirs may be simultaneously injected through a single needle cannula by activation of a single trigger mechanism. These and other advantages will become evident from the following more detailed description. The claimed subject matter does have various advantages which, inter alia, become apparent from the description below. Particularly, as the spring drives the plunger, the need of a user applied force for performing the injection may be removed. Also, the user may use a single trigger for activating the injection of a dose which may comprise medicaments from two cartridges. Particularly, the trigger may be connected to one or more dose setting and injecting components of two different sets of components. One set of components may contribute to the dose setting and injecting operation for one cartridge and the other set of components may be contribute to the dose setting and injecting operation for the other cartridge. Upon activation of the trigger, the spring of the respective set of components may be arranged to provide energy to drive the movement of the plunger associated with the set of components to which the spring belongs. Accordingly, two springs may drive the movements of separate plungers upon activation of the single trigger. The respective plunger may be arranged to force medicament out of the corresponding cartridge.

According to an aspect, an injection device is provided which comprises a dose setting and injecting assembly comprising two sets of dose setting and injecting components, which may be configured so that each set of components can operate independently during dose setting. Additionally or alternatively, the two sets of components may be configured so that both sets of components can operate simultaneously during dose injecting. Each set of components may comprise a spring and/or a plunger. A single trigger may be connected to one or more of the dose setting and injecting components, in particular such that when the trigger is activated the spring provides energy to drive the plunger. Thus, a single trigger may activate the dose injecting operation for two different sets of dose setting and injecting components.

The device may comprise a medicament housing connected to the dose setting and injecting assembly. The device and, in particular, the medicament housing may comprise a distal connector and a needle adaptor removably attached to the distal connector.

Each set of components may comprise a drive shaft and a gear. The drive shaft may be coupled to the spring. The gear may be coupled to the plunger, in particular so as to drive the plunger. Rotation of the respective gear may be converted into movement of the plunger, in particular movement of the plunger in the distal direction. Gear and drive shaft may be coupled to one another so as to transfer energy provided by the spring, preferably to transfer force exerted by the spring, from the drive shaft to the gear and from the gear to the plunger to drive the plunger. The trigger may prevent rotation of the gears of both sets of components, when it is inactive, such as during dose setting. The trigger may comprise an assembly that is in direct connection with both gears when the trigger is in a dose setting position and is disconnected from both gears when the trigger is activated to a dose injecting position. The assembly may be configured to prevent rotation of the gears in the dose setting position and to permit rotation of the gears in the dose injecting position.

According to an exemplary arrangement of the disclosure there is a, preferably semi-automatic, dual cartridge injection device, which may be capable of delivering different combinations of doses from two separate containers or cartridges of medicament, preferably via a single needle. Of course, more than two containers or cartridges may be provided in the device. The dual cartridge injection device could be reusable, where the two separate medicament containers can be replaced, or the dual cartridge injection device could be disposable, such that the two medicament containers are sealed into the device and cannot be removed. A number of different methods for combining the doses are possible. For example, either or both doses could be "fixed," either or both doses could be "variable" (user selectable), either or both doses could be "titration" (user selectable from a limited range of doses), or any combination of fixed, variable or titration doses.

The injection pen mechanism of the disclosure may contain two sets of, preferably semi-automatic, dosing mechanisms. These dosing mechanisms may be actuated simultaneously by a single combined trigger. Preferably, the device is a multiple use device, meaning that a number of injections can be administered from the same two medicament containers until one or both containers is empty. The proposed device may deliver the two medicaments through a single needle. This may therefore require a "2 to 1" needle adapter in order to connect both medicament cartridges to a single delivery needle. For a reusable device the needle adapter may be discarded and replaced regularly, possibly each time a cartridge is replaced. For each separate injection the user may manually attach a new sterile delivery needle to the "2 to 1" needle adapter. After each injection the delivery needle may be manually removed and discarded.

An alternative means of connecting both medicament cartridges to a single delivery needle is to provide a disposable "2 to 1" needle unit. For each separate injection the user will manually attach a new sterile "2 to 1" needle or needle unit. After each injection the "2 to 1" needle or needle unit should be manually removed and discarded.

The proposed dual cartridge injection device may be a "semi-automatic" injection device meaning that the liquid medication or medicament is delivered automatically, particularly through the needle, by the action of stored energy (a spring or springs) within the device. The insertion of the needle before the injection, the removal of the needle after the injection and/or the triggering of the automatic liquid injection may be performed manually by the user. The user may also be responsible for "recharging" the dose spring(s) between doses. This may be accomplished as part of the dose setting procedure.

The first step to operate the dual device may be to attach a "2 to 1" needle adapter. In a preferred embodiment the adapter will be a disposable component, however, it is expediently designed so that it can be reused for multiple injections before it must be discarded. The delivery needle, as mentioned above may be replaced after every injection. The delivery needle may attach to a hub that is integral to the adapter. The user may "set a dose" on both sides of the device individually, for example, by turning each of the separate dose dials. The user can set the two dose dials completely independently of the other, for example, both sides could be set to equal doses, different doses, or one dial could be left at 0 while a dose is set on the other dial.

In one embodiment, one or both of the medicament cartridges can be used with a "fixed" dose. In this case the dose setting step may be accomplished with a single dial in a single user step. For example a single dial could be internally geared such that it sets the "fixed" dose on both sides of the device. In a further example, for a device with one side variable and one side fixed, the fixed dose could be set by an initial rotation of the single dose dial and further rotation of the dose dial could then be used to set the variable dose. The triggering of the device will likewise occur to the user as a single step. The user will press, slide, rotate, or otherwise activate a single trigger, e.g. a trigger button, that will release both dosing mechanisms at the same time. Once the trigger is released, each side of the mechanism acts independently to cause the set dose of medicament to flow from each medicament container and preferably into the 2 to 1 needle adaptor and eventually to the injection site through the single delivery needle.

In the case of a reusable injection device, after one or both medicament containers or cartridges have been emptied the user will be able to reset the injection device to its initial position. First, the user may remove the 2 to 1 needle adapter. Then, the user may remove one or both of the cartridge holders, then reset one or both plungers or piston rods to a starting position, insert one or both new cartridges of medicament, and then reassemble the cartridge holder and, preferably, a new 2 to 1 adaptor. Alternatively, the two cartridge holders could be fabricated as a single piece that could hold both cartridges.

The dual cartridge injection device of the disclosure may require a means of connecting the two medicament containers or cartridges together in order that the combined medicament can be delivered through a single needle. There are a number of methods for achieving this, for example, the use of Y-shaped needles, special manifolds, and overlapping cartridge closures, however, a preferred approach is the 2 to 1 needle adapter. This adapter comprises a body component having a needle hub at its distal end, preferably with screw threads for the attachment of a standard disposable injection pen needle. The hub is integral to the adaptor. The hub may define, in conjunction with a seal, preferably a rubber seal, a fluid channel. At the proximal end may be one or more snap features to mount the adapter to the front (distal) end of the dual cartridge device.

The seal, preferably a rubber seal, of the adaptor may create a septum to seal around the attached disposable injection pen needle and is configured to form a fluid channel. The seal may, alternatively or additionally, act to form a seal around the two needle stubs mounted in a stub mount inside the adaptor. When the adapter is attached to the dual cartridge device the two needle stubs may each pierce a septum of the enclosed medicament containers. This will put the two medicament containers in fluid communication with the fluid channel. The stub mount expediently holds the two needle stubs in position. The stub mount may, alternatively or additionally, and hold the seal, preferably a rubber seal, in the adaptor body.

The attachment of the 2 to 1 adapter may put the two medicament containers into direct fluid communication with one another. In some cases this may not be desirable because the contents of the two medicament containers will mix and may cause stability issues with the two drugs or may affect the dose accuracy from the device. In such cases, the seal or seal component, particularly the rubber seal component, may include one or more one-way check valves that will prevent fluid passing from the adapter back into the medicament containers.

Preferably, the adapter will be a disposable component, however, since it is more complex than a standard disposable injection pen needle it should be configured of materials to allow it to be used at least until the medicament in one or both of the cartridges is exhausted.

When the device is configured as a dual variable dose device the user can select the two doses individually by turning two separate dose dials. In this configuration, any mix ratio of medicaments can be achieved. The mix ratio can be easily varied between injections. Such a device could have a number of different uses, for example preparing an individually tailored mix of basal and rapid acting insulin for a patient, or providing a means to titrate two drugs very precisely.

With any of the various embodiments of the dual cartridge device it is not necessary that both medicament containers are of the same design or the same volume. If one of the two medicaments was known to be injected in much smaller volumes than the second medicament then it would be preferred that this container would be correspondingly smaller. Indeed, there may also be an advantage to having different shaped containers, as it would ensure that the user does not confuse the two medications when reloading the device.

When the device is configured as a fixed ratio dual cartridge injection device it is possible to ensure that the device will always deliver a fixed ratio of each medicament from the two medication cartridges. For example one medicament is always delivered in twice the volume of the other medicament. Combining the two dose dials into one dial component and then linking the two separate drive shaft components via a gear could achieve this result. In this manner it is possible to achieve any desired ratio of the two medicaments, which could not be varied by the user. Although losing the advantage of ratio flexibility the fixed ratio device would be simpler to use for the patient because only one dose needs to be set and it also eliminates the possibility for patient error when calculating the required fixed ratio of medicaments.

With a fixed ratio device it would also be possible to alter the size of one or both medicament containers in order to guarantee that both containers are emptied at the same time. For example, with a fixed ratio of 2:1 one container would ideally be twice the volume of the second. For a reusable device this would reduce the number of occasions that a user would have to disassemble the 2 to 1 needle adapter and the cartridge holders. For a disposable device this would mean that the user is not throwing away drug when only one cartridge is empty. If the two drive shafts are connected via a gear then it is preferred that only one dose spring be used as this would reduce the cost of the device.

There are also a large number of drugs with a broader therapeutic window where the dose does not need to be varied from patient to patient or from day to day, or where the number of different dose sizes in common usage is limited. The device may also be configured to include a number of dosing mechanisms for either one medicament container or for both. Such flexibility allows for having one dose variable, the other dose fixed, or one dose variable, the other dose a titration dose (user selects dose from a limited range of options), or both doses fixed (but both not necessarily fixed at the same dose), or both titration doses (but not necessarily the same limited range of doses), or both doses variable (user selects each dose separately).

A semi-automatic feature of the device has certain advantage over known delivery devices that rely on a user's manual pressing of an injection button, which for a dual cartridge device would require high forces. Such an example of a manual injection is described in U.S. Pat. No. 5,584,815. This creates difficulty or even pain for elderly users or those with reduced manual dexterity. Also, any shaking of the hand while pressing the dose button will cause movement of the device and needle, making the injection more painful. A semi-automatic device removes this problem. The user supplies the energy to provide the injection during the dose setting stage. This may use larger sets of muscles, arms and wrists rather than finger or thumb power, and should therefore be easier for patients. Also, the energy is applied before the needle is injected into the body. Therefore, it does not matter if there is some movement or shaking of the device.

In prior known manually driven devices it is possible that the user does not press the dose dial fully inwards and therefore may deliver an under dose. With the semi-automatic device of the disclosure the full dose may be achieved more consistently. Likewise, dose accuracy in prior devices that require pressing a manual dose button can cause the user to not behave consistently where they will press and hold the button for varying times. Different button hold times allow different expansion of the bung or piston, preferably a rubber bung or a rubber piston, within the medicament container and this has the potential to create variability between doses. The semi-automatic feature of the device eliminates this variable because the dose spring will work independently of the user. Therefore, the forces applied to the bungs or pistons of the medicament containers or cartridges during dose delivery are determined by the design of the device, irrespective of forces applied to the trigger, which may be a trigger button.

In one embodiment of the disclosure there is provided an injection device having a dose setting/injecting assembly comprising two sets of dose setting and injecting components. Each of these is configured so that each set of components can operate independently during dose setting and operate simultaneously during dose injecting. Each set of components comprises a torsional spring, a drive shaft, a gear, and a plunger. A single trigger is connected to one or more of the dose setting and injecting components such that when the trigger is activated at least one of the torsional springs unwinds driving a plunger into a cartridge of medicament. The device also has a medicament housing connected to the dose setting/injecting assembly, which on its distal end has a connector for attaching a needle adaptor. This adaptor is removably attached and accepts a double-ended needle assembly, such as a disposable injection pen needle.

In the following text, a set of particularly advantageous aspects of the injection device is provided by making use of numbers to facilitate making references to the respective aspects.

1. An injection device comprising the following in combination,
   a. a dose setting/injecting assembly comprising,
      i. two sets of dose setting and injecting components configured so that each set of components can operate independently during dose setting and operate simultaneously during dose injecting, where each set of components comprises a torsional spring, a drive shaft, a gear, and a plunger;
      ii. a single trigger connected to one or more of the dose setting and injecting components such that when the trigger is activated the torsional spring unwinds driving the plunger into a cartridge of medicament;
   b. a medicament housing connected to the dose setting/injecting assembly having a distal connector; and
   c. a needle adaptor removably attached to the distal connector.
2. The injection device of aspect 1 wherein the medicament housing holds two cartridges of medicament.
3. The injection device of aspect 1 wherein the medicament housing comprises two separate compartments with each holding a cartridge of medicament.
4. The injection device of aspect 1 wherein the needle adaptor comprises a body having an internal stub mount containing two needle stubs in fluid communication with a fluid channel in fluid communication with a septum piercable by a double ended disposable needle assembly.
5. The injection device of aspect 1 where the needle adaptor has two needle stubs that are configured to pierce two septums positioned in two cartridges located in the medicament housing.
6. The injection device of aspect 1 where the distal connector is non-threaded.
7. The injection device of aspect 1 wherein the trigger comprises an assembly that is in direct connection with both gears when the trigger is in a dose setting position and is disconnected from both gears when the trigger is activated to a dose injecting position.

8. The injection device of aspect 1 where dose setting components have only a single dose dial that is configured to simultaneously set doses for two containers of medicament contained in the medicament housing.

9. An injection device comprising the following in combination,
   a. a dose setting/injecting assembly comprising,
      i. two sets of dose setting and injecting components configured so that each set of components can operate independently during dose setting and operate simultaneously during dose injecting, where each set of components comprises a torsional spring, a drive shaft, a gear, and a plunger;
      ii. a single trigger connected to one or more of the dose setting and injecting components such that when the trigger is activated the torsional spring unwinds driving the plunger into a cartridge of medicament;
   b. a medicament housing connected to the dose setting/injecting assembly having a distal connector; and
   c. a needle adaptor removably attached to the distal connector, wherein one set of dose setting components is configured to set only a predetermined fixed dose.

Features describe above or below in connection with different aspects, embodiments etc. may, of course, be combined with features described in connection with other aspects, embodiments etc. or with a combination of such features even if such a combination is not explicitly described herein.

The advantages mentioned above as well as other advantages of various aspects of the present disclosure will become apparent to those of ordinary skill in the art by reading the following detailed description, with appropriate reference to the accompanying drawings.

Exemplary embodiments are described herein with reference to the drawings, in which.

Figure 1:
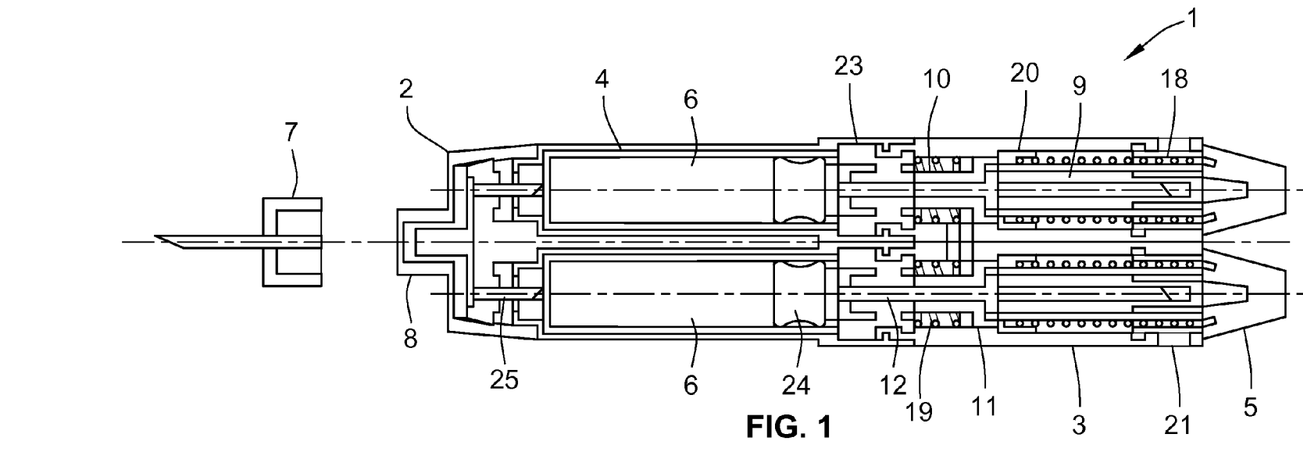
FIG. 1 illustrates one possible embodiment of the dual cartridge injection device of the disclosure.

A schematic cross section of one embodiment of the dual cartridge injection device of the disclosure is illustrated in FIG. 1. The device comprises three main assemblies: a 2 to 1 needle adaptor 2; a dose setting/injecting assembly; and a cartridge holder 4. The dose setting/injecting assembly may be arranged within a body 3. The dose setting and cartridge holder assemblies of this disclosure are similar in design and operation to that for the single cartridge pen that is described in U.S. Pat. No. 5,104,380 with significant differences. Those differences, to name a few, being that this disclosure requires a cartridge holder capable of holding two cartridges of medicament or alternatively two separate cartridge holders, the need for two separate dose setting mechanisms, and the need for a 2 to 1 needle assembly. The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group-Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Disposable injection needle assembly 7 is preferably a standard disposable injection pen double-ended needle having a threaded female hub that can attach to a male hub 8 of the 2 to 1 adaptor 2. The setting of doses within injection device 1 is controlled by the interaction of the two drive shafts 9, each of which is preferably permanently connected to one of the dose dials 5. Also involved in setting and delivery of doses are two gears 10 and a single trigger 11. During dose setting the gears are prevented from rotation by components of the trigger. Each drive shaft features a ratchet arm 13 (see FIG. 3) that engages teeth 14 on an inner surface 17 of each gear. Each tooth of the gear corresponds to one index of the dose dial. Movement of the plunger 12 is achieved by energy stored in a helical torsional spring 18, which is twisted as the dose of medicament to be injected from each cartridge is set by rotation of each dose dial 5. The dose dial can turn about a graduated sleeve or the drive shaft may contain printed graduations. Body 3 has lenses or windows 21 through which graduations on the sleeves or shafts can be read to show the angle through which the dose dials have been turned, which corresponds to the set dose.

Figure 3:
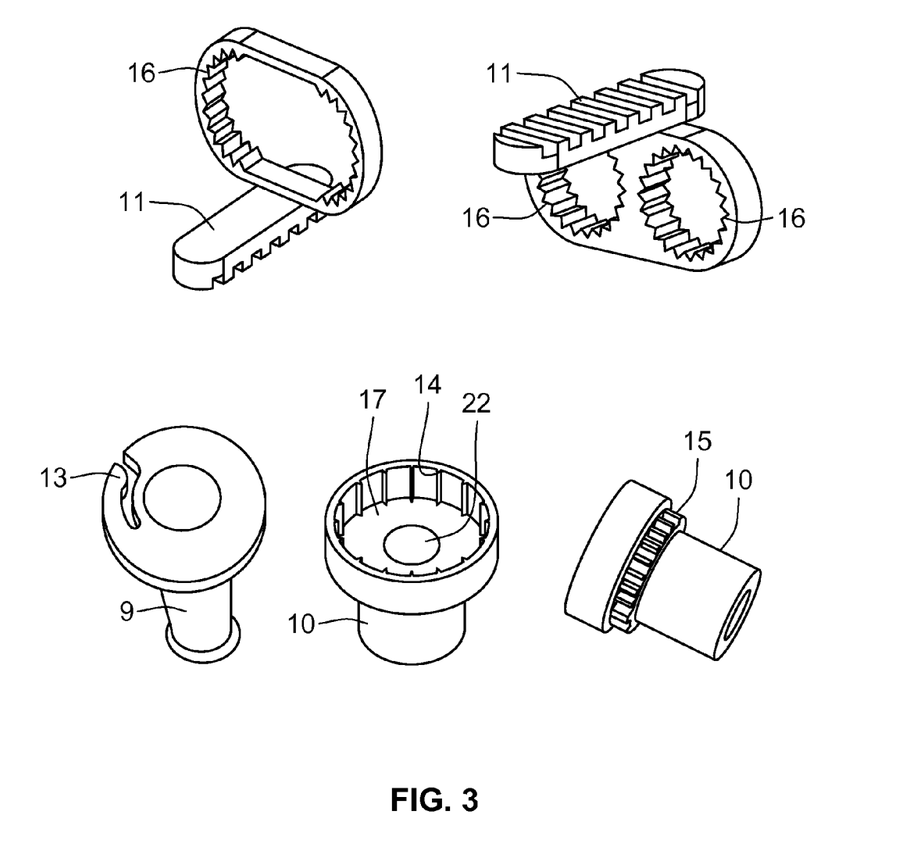
FIG. 3 illustrates possible embodiments of the drive shaft, gear and trigger of the dose setting assembly of the disclosure.

When dialing a dose the user rotates one of the dose dials 5, which causes the connected drive shaft 9 and ratchet arm 13 to rotate and click over the desired number of teeth 14 in stationary gear 10. Rotating the dose dial 5 also stores torsional energy within the corresponding dose spring 18 that is fastened to the dose dial. This stored torsional energy is used to automatically deliver the medicament dose when trigger 11 is pressed or otherwise activated causing the spring to unwind and returning the dose dial and drive shaft to the initial zero position. When the trigger 11 is activated, teeth 16 disengage from teeth 15 on both gears 10 and the respective gear becomes free to rotate with drive shaft 9.

The stored energy of the dose spring drives the drive shaft in rotation, which in turn rotates the gear. The gear 10 has a central threaded opening 22 that is in threaded engagement with plunger 12. The plunger is prevented from rotation by features in reset dial 23. Preferably, the reset dial 23 contains two protrusions (not shown) that consist of opposed flats which engage two longitudinal grooves on opposed sides along the length of the drive plunger 12. When the corresponding cartridge holder 4 is attached to the body 3 the reset dial 23 is prevented from rotation relative to the body 3. Thus, when the cartridge holder 4 is connected to the body 3 rotation of the drive plunger 12 is prevented. Because the drive plunger 12 cannot rotate and the gear 10 cannot move axially, the rotation of the gear 10 causes the drive plunger 12 to advance along its thread that is engaged with gear 10, particularly with the thread in gear 10, in an axial distal direction exerting force on piston 24 inside cartridge 6. This causes the pressure in the cartridge to increase and liquid medicament is dispensed from the distal end of the cartridge into needle stub 25, which is part of the 2 to 1 adaptor 2. If the trigger 11 is released at any point during the delivery of the set dose, teeth 15 and 16 will re-engage stopping the rotation of gear 10 and thus stopping the delivery of medicament. Pressing the trigger again will continue the delivery until all of the dialed units have been delivered. The injection of medicament is complete when the dose dial 5 reaches a rotational stop with respect to the body 3. This stop position corresponds to the "zero dose selected" position of the dose dial 5.

Figure 4:
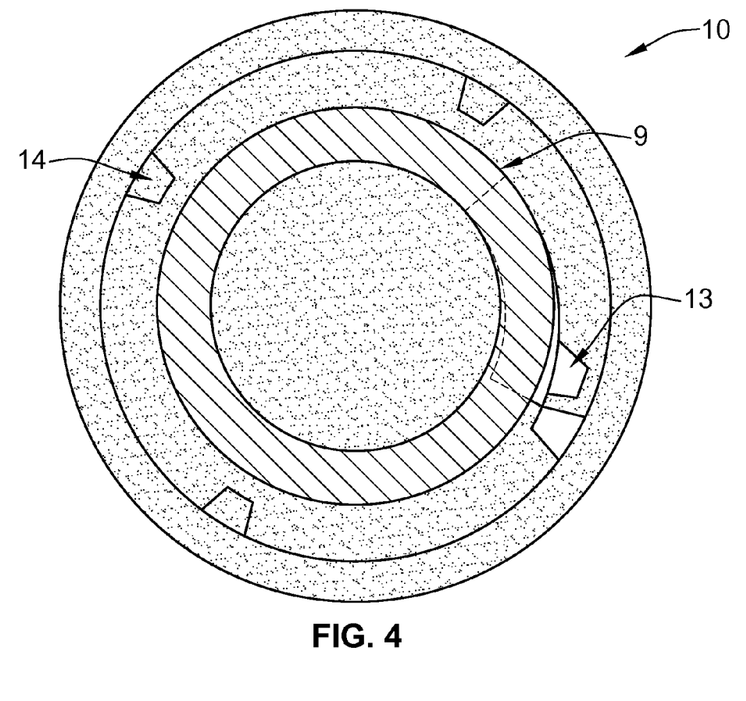
FIG. 4 illustrates a cross sectional view of one side of the device showing a fixed dose stationary gear and drive shaft.

As mentioned, the device can be a completely variable dose or completely fixed dose device or a combination of fixed and variable dose. When it is desired to set one or both of the medicaments one or both of the stationary gears 10 may be modified by changing the number of gear teeth 14 to remove the majority of the teeth from the gear. One embodiment of this fixed dose gear is shown in FIG. 4. The teeth 14 that remain are evenly spaced around the circumference of stationary gear 10. The angle between these remaining teeth corresponds to the angle that the drive shaft 9 will be rotated when the fixed dose is delivered. For example, if the gear contains four teeth then the angle between them will be 90°. If the drive plunger 12 thread pitch is 6 mm then a 90° rotation will cause the plunger to advance by a "fixed" increment of 1.5 mm. By appropriate design of the number of gear teeth, and the thread pitch between the gear and the plunger, the nominal volume of the fixed dose can be altered.

If the user fails to rotate the dose dial 5 by an angle sufficient to engage the ratchet arm 13 of the drive shaft 9, then the dose will not be set. The dose spring will rotate the dose dial and drive shaft back to the zero unit position of the dose dial. Therefore, it will be impossible for the user to set any dose below the "fixed dose" determined by the spacing of the gear teeth. The fact that the dose dial immediately rotates back to zero units, rather than remaining at the marker for the fixed dose, will alert the user to the fact that the dose was not properly set. This should prevent the user from attempting to deliver a zero dose. This places an ergonomic limit on how far the user can be expected to rotate the dose dial in one movement. It is therefore preferred that there should be a minimum of two gear teeth. This would mean that the maximum rotation the user would have to apply would be 180°.

The maximum dose of the device can be limited by adding features that will limit the rotation of the dose dial (and hence drive shaft). This limit will be designed to suit the pitch of the gear teeth and prevent the user from dialing beyond a second tooth. A number of options exist for adding rotation restricting features, for example features could be added to the dose dial & body or to the drive shaft & body. A small amount of rotation over travel is required in order to guarantee that the ratchet arm will engage. Therefore the rotational limit of the dose dial would be set to an angle slightly greater than the angle between the gear teeth. However, this over travel does not contribute to any dose accuracy error of the pen because when the user releases the dose dial the dose spring will immediately rotate the dose dial and drive shaft back until the ratchet arm contacts the gear tooth. Given that the trigger is not pressed at this point then the rotation of the drive shaft does not rotate the gear and hence no medicament is dispensed.

If the device 1 is a fixed mix ratio device as described further above which is configured to dispense liquid medicament comprising a fixed mix ratio of the medicaments from the two cartridges 6, the drive shafts 9 may be coupled to each other by an additional gear (not explicitly shown). This may be done, because the ratio of the distances by which the two plungers have to be advanced for achieving a fixed mix ratio may also be fixed. Thus, the different distances by which the plungers 12 are displaced could be set by choosing different pitches in the threads of the plungers. Rotation of the drive shafts 9 by the same angle due to the coupling by the additional gear would then still cause different displacement distances of the plungers. A combined dose spring 18 may then be used instead of two separate dose springs 18.

The dual cartridge device of the disclosure contains two sets of the dose setting mechanism (dose dial 5, drive shaft 9, gear 10) and two sets of the dose delivery mechanism (dose spring 18, spring retainer 20, drive plunger 12). If simultaneous injection of medicaments from each separate cartridge 6 is required, then each delivery mechanism must be activated by a single trigger 11. Although there could be two separate trigger springs 19, it is preferred that they are combined into a single trigger spring component. When the trigger is not being held by the user in the activated position the trigger spring 19 pushes the trigger 11 into engagement with gear teeth 15 on the outside of the two gear components 10. This will hold both gear components 10 in a fixed rotational position while the dose is set. The user can then set the two doses individually by rotating the two dose dials 5, which in turn rotate the two drive shafts 9. In some configurations there maybe only a single dose dial that the user can operate. In such configurations, setting the single dose dial will set doses for both medicaments because internally one dose setting assembly is slaved off of the other that is connected to the single dose dial.

Figure 5:
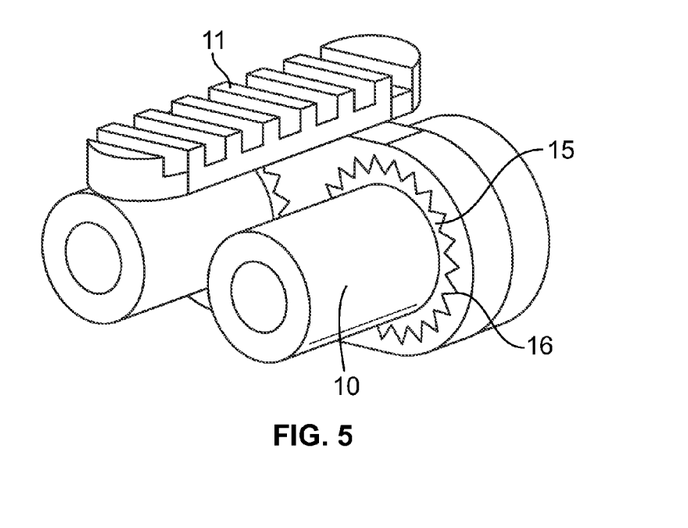
FIG. 5 illustrates one possible embodiment of the gear and trigger of the dose setting assembly of the disclosure.
Figure 6:
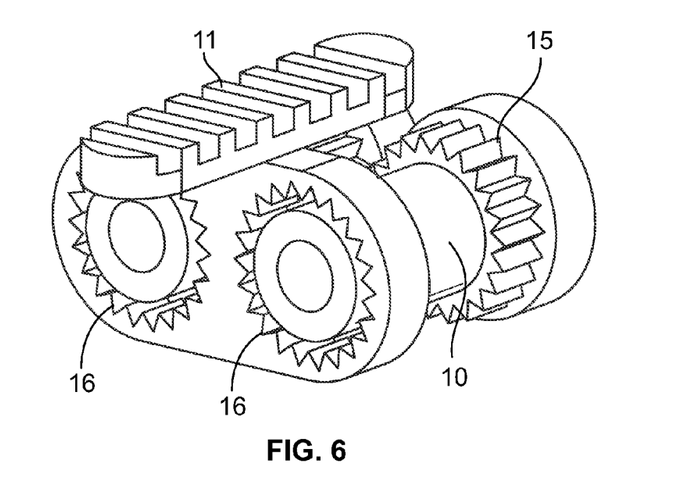
FIG. 6 illustrates another possible embodiment of the gear and trigger of the dose setting assembly of the disclosure.

When the user is ready to deliver the injection, the trigger 11 is activated, preferably pressed forwards, compressing the trigger spring 19. The outer teeth of the two gears 10 are both released by the trigger 11 and are each now free to rotate independently of each other. (See FIG. 5) FIG. 3 shows two possible designs of trigger 11, each having one or more sets of teeth 16 that engage corresponding teeth 15 on each of the two gears 10. Provided a dose has been set, each gear 10 will be driven by its respective dose spring 20. Each gear 10 is threaded to its respective drive plunger 12, and rotation of the gear 10 will cause that plunger 12 to advance. Releasing the trigger 11 will allow the trigger spring 19 to push the trigger 11 back into engagement with the teeth 15 of the two gears. (See FIG. 4) If the injection has not been completed this will cause the injection to stop. The dose remaining to be injected will be displayed on the two dose dials. Pressing the trigger again will continue the injection.

Upon injection, axial movement of the plungers 12 along the quick pitch thread accompanies rotation of the two gears 10 and drive shafts 9 since the plungers cannot rotate in the reset dial 23. Thus, the plungers are driven into the cartridges, expelling the pre-set doses of medicament from each respective cartridge. The injection of medicament is complete when both dose dials 5 reach their rotational stops with respect to the body 3. These stop positions correspond to the "zero dose selected" position of each dose dial 5. When the two dose dials 5 each reach their rotational stops on the pen body, the plungers remains part-way along the inside of the cartridges. The procedure can be repeated until each cartridge is exhausted, after which the cartridges can be replaced by removing the cartridge holder the dose dialing assembly.

In some cases, the requirement to hold down the trigger until the injection is complete may be considered undesirable and therefore an alternate embodiment would include a configuration that prevents the trigger from reengaging with the gears even though the user releases the trigger. This can be accomplished by including a detent mechanism whereby pressing the trigger causes it to bump-over a detent so that it will remain in the forwards position even if the user releases the trigger button. The detent could be designed to disengage only when the two drive shafts or dose dials have returned to their initial, zero, positions. This would enable the complete injection to be delivered with only a single press of the trigger (without the need to hold the trigger forwards). A further advantage would be that the return of the trigger to its initial position would give the user additional visual and audible feedback to indicate that the dose is complete.

The reset dial 23 not only prevents the plunger 12 from rotation during that movement, but it also acts as a means for retracting the drive plunger back into the body 3 thus resetting the device. When the cartridge holder 4 is attached to the body 3 the reset dial 23 is restrained against rotation in the body 3 by a locking member fitted into the reset dial 23. When the cartridge holder 4 is removed the locking member is unrestrained and allows rotation of the reset dial. The drive plunger 12 is prevented from rotation relative to the reset dial 23 by the engagement of reset dial protrusions and drive plunger longitudinal grooves. The drive plunger 12 is threadedly engaged to the gear 10. Gear 10 is fixed in rotation relative to the body 3 by the engagement of gear teeth 15 and trigger teeth 16. Rotation of the reset dial 23 causes the drive plunger 12 to rotate which causes it to wind up the thread in the gear 10, thus retracting the drive plunger back into the body 3.

Figure 2:
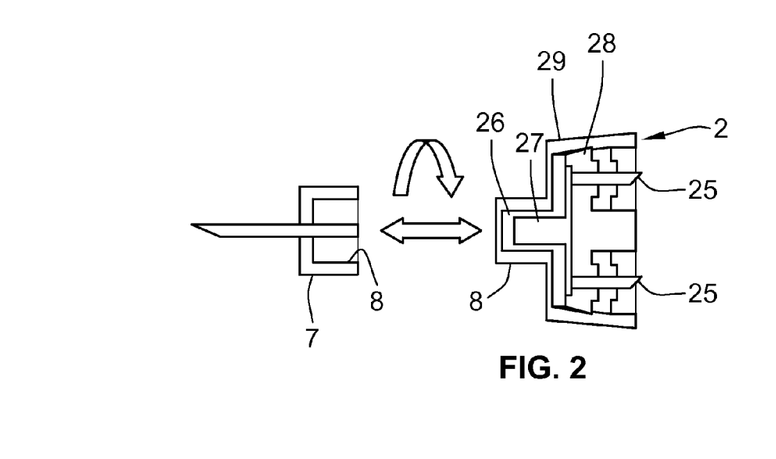
FIG. 2 illustrates a detailed schematic of one possible embodiment of the 2 to 1 needle adaptor of the disclosure.

FIG. 2 illustrates a detailed view of one possible embodiment of the 2 to 1 needle adaptor 2 of the disclosure. The adaptor comprises a body 29 having a needle hub 8 containing male threads configured to allow attachment of a double-ended needle assembly 7. Inside body 29 is a pierceable seal 26, e.g. a rubber seal, that defines a fluid channel 27 where medicament from cartridges 6 combine and flow through needle assembly 7. The seal 26 may create a septum of the adaptor. The adaptor also contains stub mount 28 that holds needle stubs 25 with the body in an axial configuration so they can pierce the cartridge septums at the distal ends of cartridges 6 when the adaptor is attached to the cartridge holder 4. The seal 26 may also act to form a seal around the two needle stubs mounted in the stub mount 28. At the proximal end of the adaptor 2 and, particularly, of the body 29 may be one or more snap features or other means to mount or connect the adaptor to the front (distal) end of the dual cartridge device. The cartridge holder 4 may be provided with a distal connector (not explicitly shown), e.g. comprising corresponding snap features, which interacts with the means of the adaptor 2 to mount or connect the adaptor to the cartridge holder. In particular, the distal connector may be non-threaded.

The attachment of the 2 to 1 adaptor 2 will put the two medicament cartridges or containers into direct fluid communication with one another. In some cases this may not be desirable because the contents of the two medicament cartridges will mix and may cause stability issues with the two drugs or may affect the dose accuracy from the device. In such cases, the seal 26 can include one or a plurality of one-way check valves (not explicitly illustrated) that will prevent fluid passing from the adaptor 2 back into the medicament cartridges 6.

The adaptor 2 may be a disposable adaptor, which may be used at least until the medicament in one or both cartridges 6 is exhausted.

The cartridges 6 may have different sizes and/or shape, in particular different exterior shapes (not explicitly illustrated). Discriminability of the cartridges 6 may thus be increased. Furthermore, the medicament contained in one cartridge 6 may be provided in a different amount, e.g. in a cartridge of smaller volume, than the medicament contained in the other cartridge 6. This is particularly advantageous if one of the medicaments is known to be needed in an amount which is less than the amount which is required of the other medicament.

Exemplary embodiments of the present disclosure have been described. Those skilled in the art will understand, however, that changes and modifications may be made to these embodiments without departing from the true scope and spirit of the subject matter which is defined by the claims.

REFERENCE NUMERALS 1 injection device
2 needle adaptor
3 body
4 cartridge holder
5 dose dial
6 cartridge
7 needle assembly
8 needle hub
9 drive shaft
10 gear
11 single trigger
12 plunger
13 ratchet arm
14 teeth
15 teeth
16 teeth
17 inner surface
18 dose spring
19 trigger spring
20 spring retainer
21 window
22 opening
23 reset dial
24 piston
25 needle stub
26 pierceable seal
27 fluid channel
28 stub mount
29 body

The invention claimed is:

1. An injection device comprising,
 a dose setting and injecting assembly comprising,
  i. two sets of dose setting and injecting components configured so that each set of components can operate independently during dose setting and both sets of components can operate simultaneously during dose injecting, where each set of components comprises a spring, a plunger, a drive shaft, and a gear;
  ii. a single trigger connected to one or more of the dose setting and injecting components such that when the trigger is activated the spring provides energy to drive the plunger, wherein the trigger comprises teeth that are in direct connection with both gears when the trigger is in a dose setting position and are disconnected from both gears when the trigger is activated to a dose injecting position.

2. The injection device of claim 1 comprising a medicament housing connected to the dose setting and injecting assembly, the injection device further comprising a distal connector and a needle adaptor removably attached to the distal connector.

3. The injection device of claim 2 where the distal connector is non-threaded.

4. The injection device of claim 2 wherein the medicament housing holds two cartridges of medicament.

5. The injection device of claim 4, wherein the medicament housing comprises two separate compartments with each compartment holding one cartridge of medicament.

6. The injection device of claim 2 wherein the needle adaptor has two needle stubs.

7. The injection device of claim 6 wherein the needle stubs are configured to pierce two septums positioned in two cartridges located in the medicament housing.

8. The injection device of claim 6 wherein the needle adaptor comprises a body having an internal stub mount containing the two needle stubs in fluid communication with a fluid channel, which is in fluid communication with a septum piercable by a double ended disposable needle assembly.

9. The injection device of claim 1 wherein the dose setting components have only a single dose dial that is configured to simultaneously set doses for two cartridges of medicament.

10. The injection device of claim 1 wherein the device is configured such that the energy for driving the plunger is stored in the spring during dose setting.

11. The injection device of claim 1 wherein the spring is a torsional spring which unwinds when the trigger is activated.

12. The injection device of claim 1 wherein the drive shaft is coupled to the spring, the gear is coupled to the plunger, and the trigger is arranged to prevent rotation of the gears of both sets of components during dose setting.

13. The injection device of claim 1 wherein one set of dose setting components is configured to set only a predetermined fixed dose.

* * * * *